United States Patent [19]

Pieper et al.

[11] Patent Number: 4,507,249

[45] Date of Patent: * Mar. 26, 1985

[54] PROCESS FOR MAKING DERIVATIVES OF VINYLPHOSPHONIC ACID OR VINYLPYROPHOSPHONIC ACID

[75] Inventors: Werner Pieper, Erftstadt; Werner Krause, Hürth-Knapsack, both of Fed. Rep. of Germany

[73] Assignee: Hoechst Aktiengesellschaft, Fed. Rep. of Germany

[ * ] Notice: The portion of the term of this patent subsequent to Dec. 4, 2001 has been disclaimed.

[21] Appl. No.: 472,261

[22] Filed: Mar. 4, 1983

[30] Foreign Application Priority Data

Mar. 22, 1982 [DE] Fed. Rep. of Germany ....... 3210419

[51] Int. Cl.$^3$ ................................................ C07F 9/38
[52] U.S. Cl. .................... 260/502.4 R; 260/502.4 P
[58] Field of Search .................. 260/502.4 R, 502.4 P

[56] References Cited

U.S. PATENT DOCUMENTS

| | | | |
|---|---|---|---|
| 2,230,371 | 2/1941 | Bolton | 260/502.4 R |
| 2,254,124 | 8/1941 | Stevens et al. | 260/502.4 R |
| 2,279,501 | 4/1942 | Dickey et al. | 260/502.4 R |
| 2,365,466 | 12/1944 | Hamilton | 260/502.4 R |
| 2,686,803 | 8/1954 | Stayner | 260/502.4 R |
| 2,693,482 | 11/1954 | Stayner | 260/502.4 R |
| 2,694,684 | 11/1954 | Rogers et al. | 260/502.4 R |
| 4,388,252 | 6/1983 | Dursch et al. | 260/502.4 R |

Primary Examiner—J. E. Evans
Attorney, Agent, or Firm—Connolly and Hutz

[57] ABSTRACT

The disclosure relates to a process for making derivatives of vinylpyrophosphonic acid, wherein a ketone is reacted with tetraphosphorus hexoxide ($P_4O_6$) in the presence of a catalytically active proportion of a proton-yielding substance at elevated temperature. Vinylphosphonic acid derivatives are obtained by hydrolyzing the vinylpyrophosphonic acid derivatives with an equivalent proportion of water. More particularly, the ketone used is a compound of the following general formula

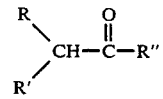

in which either R stands exclusively for a halogen and R' either stands for a halogen or hydrogen, a halogen-substituted or unsubstituted alkyl, aryl, alkaryl or aralkyl group having from 1 to 18 carbon atoms, and R" stands for an alkyl, aryl, alkaryl, aralkyl or alkenyl group having from 1 to 18 carbon atoms, or R" stands exclusively for an alkenyl group having from 2 to 18 carbon atoms and R and R' being identical or different each stand for hydrogen or a halogen or a halogen-substituted or unsubstituted alkyl, aryl, alkaryl or aralkyl group having from 1 to 18 carbon atoms.

14 Claims, No Drawings

PROCESS FOR MAKING DERIVATIVES OF VINYLPHOSPHONIC ACID OR VINYLPYROPHOSPHONIC ACID

CROSS REFERENCE TO RELATED APPLICATION

Our copending application Ser. No. 390,190, filed June 21, 1982, contains technologically related subject matter.

The present invention relates to a process for making derivatives of vinylphosphonic acid or vinylpyrophosphonic acid.

Vinylphosphonic acid, vinylpyrophosphonic acid and the derivatives of these acids are of commercial interest as they can be polymerized to give compounds of high molecular weight or can be made together with other polymerizable vinyl compounds into a copolymer.

Heretofore, they have been made by reacting a ketone with $PCl_3$. This process which is carried out in a plurality of operational steps involving the formation of various intermediate products entails considerable adverse effects and corrosiveness originating from chlorine which is separated in the form of hydrogen chloride or acetyl chloride.

It has also been proposed to make derivatives of vinylphosphonic acid or vinylpyrophosphonic acid by reacting a ketone with tetraphosphorus hexoxide ($P_4O_6$) in the presence of catalytic proportions of a proton-yielding substance at elevated temperature and, in the event of the products desired to be produced being vinylphosphonic acid derivatives, hydrolyzing the vinylpyrophosphonic acid derivatives first obtained with an equivalent quantity of water.

The ketones used in the process just described are compounds of the following general formula

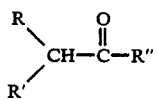

in which R and R' being identical or different each stand for hydrogen or a halogen-substituted or unsubstituted alkyl, aryl alkaryl or aralkyl group having from 1 to 18 carbon atoms, and R" stands for an alkyl, aryl, alkaryl or aralkyl group having from 1 to 18 carbon atoms.

We have now unexpectedly found that the process for making derivatives of vinylphosphonic acid or vinylpyrophosphonic acid just described can also be effected by using a ketone of the above general formula (I) in which however either (a) R stands exclusively for a halogen and R' either stands for a halogen or hydrogen, a halogen-substituted or unsubstituted alkyl, aryl, alkaryl or aralkyl group having from 1 to 18 carbon atoms, and R" stands for an alkyl, aryl, alkaryl or aralkyl or alkenyl group having from 1 to 18 carbon atoms, or (b) R" stands exclusively for an alkenyl group having from 2 to 18 carbon atoms and R and R' being identical or different each stand for hydrogen or a halogen or a halogensubstituted or unsubstituted alkyl, aryl, alkaryl or aralkyl group having from 1 to 18 carbon atoms.

A preferred feature provides for use to be made of those ketones in which the halogen is chlorine or bromine.

The artisan would not have expected the ketones which are used in accordance with this invention to permit effecting the reaction just described for the following reasons: firstly, it has been described in East German patent DD-PS No. 112 763 that α-halogenocarbonyl compounds normally react with $P_4O_6$ to give pyrophosphoric acid divinylester dichlorides; secondly, α,β-unsaturated ketones have been shown (HOUBEN-WEYL: "Methoden der organischen Chemie", volume 12/1, 1963, pages 361 and 470) to react with phosphorus trichloride or phosphorous acid dialkylesters to give γ-oxoalkanephosphonic acid derivatives; finally, ketones carrying alkenyl groups would have been expected to polymerize in the presence of a proton-yielding substance.

The ketone and $P_4O_6$ should preferably be reacted in a molar ratio of at least 4:1.

It is good practice to use the proton-yielding substance in proportions of a least 0.0001 weight %, preferably 0.01 to 1 weight %, based on $P_4O_6$, and to effect the reaction at temperatures of 40 to 150° C.

The proton-yielding substances should be selected, for example, from the group consisting of water, alcohols, amines, hydrochloric acid, sulfuric acid, phosphoric acid, phosphorous acid, phosphonic acids or carboxylic acids.

A particularly advantageous feature provides for the respective final product to be used as the proton-yielding substance which permits the reaction to be carried out in the absence of foreign substances.

The process should preferably be effected by metering $P_4O_6$ into the ketone which may optionally be diluted with an inert organic solvent. Needless to say, $P_4O_6$ may also be diluted with an inert organic solvent, if desired. In order to initiate the reaction, it is necessary for the ketone to contain a catalytic proportion of a substance capable of readily yielding protons and reacting spontaneously with $P_4O_6$ with break-up of a P-O-P-bond.

The $P_4O_6$ should preferably be added continuously at elevated temperatures, especially within the range 40° to 150° C., within which $P_4O_6$ undergoes complete exothermal reaction. During the reaction, it is commonly not necessary to use additional heat as the reaction enthalpy normally permits the selected temperature to be maintained so that it is possible for the temperature to be controlled by means of the $P_4O_6$ introduction velocity.

In those cases in which highly reactive ketones are concerned, the reaction directly results in the formation of vinylpyrophosphonic acid derivatives, which are either isolated as such or, after addition of the necessary stoichiometric quantity of water, are made into corresponding vinylphosphonic acid derivatives.

In all other cases, the polymeric crude product first obtained by reacting the ketone with $P_4O_6$ is subjected to thermal after-treatment. To this end, the crude product is heated over a period of 10 to 60 minutes to temperatures lying between reaction temperature and 250° C. The minimum temperature to be used depends on the reactivity of the particular ketone used. In this manner crude vinylpyrophosphonic acid derivatives are obtained which can be converted to vinylphosphonic acid derivatives by addition of the necessary calculated quantity of water.

It is also possible for the crude product to be reacted in an autoclave with an excess of water at elevated temperatures and under elevated pressure with direct formation of vinylphosphonic acid derivatives.

As illustrated in the following Examples, the present process is a new route to phosphonic acid compounds which are readily obtainable in high yields by reacting tetraphosphorus hexoxide with ketones.

EXAMPLE 1

62 g (0.4 mol) α-chloroacetophenone (Cl—CH$_2$—CO—C$_6$H$_5$) and 0.1 g (0.00045 mol) 2-chloro-1-phenyl-vinyl-1-phosphonic acid heated to 150° C. and placed in a 250 ml multi-necked flask provided with a stirrer, thermometer, reflux condenser and dropping funnel were admixed dropwise under inert gas and while stirring with 22 g (0.1 mol) P$_4$O$_6$ so that the temperature did not exceed 155° C. After a post-reaction period of about 5 minutes, 100 ml xylene was added and 5 ml (0.3 mol) water was added at about 110° C. Next, water in excess was removed by azeotropic distillation. On allowing the solution to cool, 2-chloro-1-phenyl-vinyl-1-phosphonic acid commenced crystallizing out of which 66 g (0.3 mol; 75%) was isolated after filtration and washing the filter residue with xylene and hexane. The melting point was 134°–138° C.

EXAMPLE 2

157 g (1.6 mol) mesityloxide, (H$_3$C)$_2$C=CH—CO—CH$_3$, in 160 ml toluene placed in an apparatus as described in Example 1 was admixed first with 1 ml water and then dropwise with 88 g (0.4 mol) P$_4$O$_6$, the boiling temperature of toluene being reached without additional supply of heat. $^{31}$P-NMR-spectroscopy indicated that the toluenic solution contained 50% 4-methylpenta-2,4-diene-2-pyrophosphonic acid together inter alia with 30% 4-methylpenta-2,4-diene-2-phosphonic acid, based on the phosphorus used. This crude product was hydrolyzed with 100 ml water and the aqueous phase was found to contain about 80% of the phosphorus used, in the form of 4-methylpenta-2,4-diene-2-phosphonic acid. This aqueous solution was heated for 2 hours under its own pressure to 250° C. in an autoclave and constitutionally isomeric 2-hydroxy-3,5,5-trimethyl-2-oxo-1-oxaphospholene was obtained as the final product which crystallized out from the aqueous solution; it could be isolated in a yield of about 40% by recrystallizing it with water and glacial acetic acid, respectively.

We claim:

1. A process for making phosphonic or pyrophosphonic acids from ketones comprising:
reacting a ketone of the formula

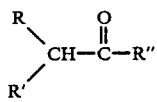

in which either
(a) R stands exclusively for a halogen, R' either stands for a halogen or hydrogen, a halogen-substituted or unsubstituted alkyl, aryl, alkaryl or aralkyl group having from 1 to 18 carbon atoms, and R'' stands for an alkyl, aryl, alkaryl, aralkyl or alkenyl group having from 1 to 18 carbon atoms, or
(b) R'' stands exclusively for an alkenyl group having from 2 to 18 carbon atoms and R and R' being identical or different each stand for hydrogen or a halogen or a halogen-substituted or unsubstituted alkyl, aryl, alkaryl or aralkyl group having from 1 to 18 carbon atoms, with tetraphosphorous hexoxide (P$_4$O$_6$) in the presence of at least 0.0001 weight %, based on the tetraphosphorus hexoxide of a proton donor or an amine at elevated temperatures, and obtaining a phosphonic or pyrophosphonic acid reaction product having a substituted vinyl group, the said substituted vinyl group being substituted by R'' on one of the carbons of the vinyl group, and, if R and R' are not hydrogen, by R and R', on the other carbon of the vinyl group.

2. A process according to claim 1, wherein the halogen is chlorine or bromine.

3. A process according to claim 1, wherein the vinylpyrophosphonic acid reaction product is isolated as such.

4. A process according to claim 1, wherein a vinylpyrophosphonic acid product is obtained as the reaction product and is hydrolyzed to the corresponding vinylphosphonic acid, which is recovered as the final product.

5. A process according to claim 4, comprising the steps of:
reacting a ketone of the formula

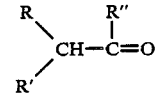

with phosphorous hexoxide in the presence of at least 0.0001 weight % of a proton donor at elevated temperatures thereby obtaining an R, R', and R''-substituted pyrophosphonic acid reaction product, R, R' and R'' having the previously defined meanings, and hydrolyzing said pyrophosphonic acid product with an equivalent of water to obtain the corresponding vinylphosphonic acid,

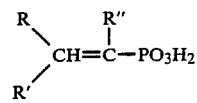

R, R', and R'' having the previously defined meanings, and recovering said corresponding vinylphosphonic acid.

6. A process according to claim 5 wherein, in said ketone, R is chlorine, R' is H, and R'' is an aryl group; or, R'' is alkenyl and R and R' are hydrogen.

7. The process according to claim 1, wherein the P$_4$O$_6$ and ketone are reacted in a molar ratio of at least 4:1.

8. The process according to claim 1, wherein the proton donor is used in proportions of 0.1 to 1.0 weight %, based on P$_4$O$_6$.

9. The process according to claim 1, wherein the reaction is effected at temperatures of 40° to 150° C.

10. The process according to claim 1, wherein the proton donor is a member selected from water, alcohols, hydrochloric acid, sulfuric acid, phosphoric acid, phosphorous acid, phosphonic acids or carboxylic acids.

11. The process according to claim 1, wherein the proton donor is the vinylphosphonic acid or vinylpyrophosphoric acid intended as the product of the reaction between the ketone and $P_4O_6$.

12. The process according to claim 1, wherein the reaction product is heat-treated at temperatures between the reaction temperature and 250° C.

13. The process according to claim 12, wherein the heat treatment is followed by addition of water and conversion of the reaction product to a vinylphosphonic acid.

14. The process as claimed in claim 1, wherein the reaction product is reacted with water under pressure in an autoclave with direct formation of a vinylphosphonic acid.

* * * * *